US008431153B2

(12) United States Patent
Shukla

(10) Patent No.: US 8,431,153 B2
(45) Date of Patent: Apr. 30, 2013

(54) BIOACTIVE COMPOSITION FOR THE TREATMENT OF THE HIV/AIDS, METHOD FOR MANUFACTURING AND USING THE SAME

(75) Inventor: Mukesh Harilal Shukla, Surendranagar (IN)

(73) Assignee: Celebrity Biogens, LLC, Rockland, MA (US)

( * ) Notice: Subject to any disclaimer, the term of this patent is extended or adjusted under 35 U.S.C. 154(b) by 283 days.

(21) Appl. No.: 12/864,961

(22) PCT Filed: Nov. 6, 2008

(86) PCT No.: PCT/IN2008/000756
§ 371 (c)(1),
(2), (4) Date: Jul. 28, 2010

(87) PCT Pub. No.: WO2010/029562
PCT Pub. Date: Mar. 18, 2010

(65) Prior Publication Data
US 2011/0003841 A1    Jan. 6, 2011

(30) Foreign Application Priority Data
Sep. 9, 2008  (IN) .......................... 1899/MUM/2008

(51) Int. Cl.
*A61K 9/20*   (2006.01)
*A61K 9/48*   (2006.01)
*A61K 9/14*   (2006.01)
*A61K 31/12*  (2006.01)
*A61K 31/19*  (2006.01)
*A61K 31/44*  (2006.01)

(52) U.S. Cl.
USPC ........... 424/464; 424/451; 424/489; 514/679; 514/690; 514/574; 514/283; 514/280

(58) Field of Classification Search ................ 514/679, 514/690, 574, 283, 280; 424/489, 464, 451
See application file for complete search history.

(56) References Cited

U.S. PATENT DOCUMENTS

| | | | | |
|---|---|---|---|---|
| 5,916,919 A | * | 6/1999 | Xu et al. ................. | 514/557 |
| 6,264,995 B1 | | 7/2001 | Newmark | |
| 7,060,294 B2 | * | 6/2006 | Batra et al. ............. | 424/464 |
| 2002/0094991 A1 | * | 7/2002 | Gallaher .................. | 514/283 |
| 2005/0266105 A1 | | 12/2005 | Ashiagbor | |
| 2006/0020027 A1 | | 1/2006 | Balasubramanyam | |
| 2007/0298132 A1 | | 12/2007 | Tin-Wa | |

FOREIGN PATENT DOCUMENTS

| | | | |
|---|---|---|---|
| JP | 03/095116 | * | 4/1991 |
| WO | WO 94/04139 | * | 3/1994 |
| WO | WO2008103346 | | 8/2008 |

OTHER PUBLICATIONS

Jordan et al. "Systematic review and meta-analysis of evidence for increasing number of drugs in antiviral combination therapy," BMJ, vol. 324, Mar. 2002, pp. 1-10.*
Ma C. et al.: "Inhibitory Effects of Ursolic Acid Derivatives from *Cynomorium songaricum*, and Related Triterpenes on Human Immunodeficiency Viral Protease", Phytotherapy Research, John Wiley & Sons Ltd. Chichester, GB, vol. 12, No. 1, Jan. 1, 1998, pp. S138-S142.

* cited by examiner

*Primary Examiner* — Shengjun Wang
(74) *Attorney, Agent, or Firm* — Bay State IP, LLC

(57) ABSTRACT

The present invention is about a bioactive composition for the treatment of HIV, particularly by the removal of the most prominent HIV antigen glycoproteins. The present invention further relates to the method for making and using such composition.

**19

BIOACTIVE COMPOSITION FOR THE TREATMENT OF THE HIV/AIDS, METHOD FOR MANUFACTURING AND USING THE SAME

CROSS REFERENCE TO RELATED APPLICATION

This application is for entry into the U.S. National Phase under §371 for International Application No. PCT/IN2008/000756 having an international filing date of Nov. 6, 2008, and from which priority is claimed under all applicable sections of Title 35 of the United States Code including, but not limited to, Sections 120, 363 and 365(c), and which in turn claims priority under 35 USC 119 to Indian Patent Application No. 1899/MUM/2008 filed on Sep. 9, 2008.

TECHNICAL FIELD OF THE INVENTION

The present invention contemplates a bioactive composition for the treatment of HIV, particularly by the removal of the most prominent HIV antigen glycoproteins.

Additionally, the present invention further describes the method for making and using such composition.

Among all the current prevailing diseases the diseases of viral origin and in that also the HIV/AIDS is the most concern for the research to cure it or to prevent it.

BACKGROUND AND RELATED ARTS

AIDS was first reported in the United States in 1981 and has since become a major worldwide epidemic. AIDS is caused by the human immunodeficiency virus, or HIV. By killing or damaging cells of the body's immune system, HIV progressively destroys the body's ability to fight infections and certain cancers. People diagnosed with AIDS may get life-threatening diseases called opportunistic infections. These infections are caused by microbes such as viruses or bacteria that usually do not make healthy people sick.

Since 1981, more than 980,000 cases of AIDS have been reported in the United States to the Centers for Disease Control and Prevention (CDC). According to CDC, more than 1,000,000 Americans may be infected with HIV, one-quarter of who are unaware of their infection. The epidemic is growing most rapidly among minority populations and is a leading killer of males of all whole world with the ages of 25 to 44.

Human Immunodeficiency Virus (HIV) presents a complex knot for scientists to unravel. After initial contact and attachment to a cell of the immune system (e.g. lymphocytes, monocytes), there is a cascade of intracellular events. The endproduct of these events is the production of massive numbers of new viral particles, death of the infected cells, and Ultimate devastation of the immune system.

In initial stage, many people will not have any symptoms when they first become infected with HIV. They may, however, have a flu-like illness within a month or two after exposure to the virus. This illness may include Fever, Headache, profound weakness, Enlarged lymph nodes (glands of the immune system easily felt in the neck and groin) these symptoms usually disappear within a week to a month and are often mistaken for those of another viral infection. During this period, people are very infectious, and HIV is present in large quantities in genital fluids.

More persistent or severe symptoms may not appear for 10 years or more after HIV first enter the body in adults, or within 2 years in children born with HIV infection. This period of asymptomatic infection varies greatly in each person. Some people may begin to have symptoms within a few months, while others may be symptom-free for more than 10 years.

Even during the asymptomatic period, the virus is actively multiplying, infecting, and killing cells of the immune system. The virus can also hide within infected cells and be inactive. The most obvious effect of HIV infection is a decline in the number of CD4 positive T (CD4+) cells found in the blood—the immune system's key infection fighters. The virus slowly disables or destroys these cells without causing symptoms.

As the immune system becomes more debilitated, a variety of complications start to take over. For many people, the first signs of infection are large lymph nodes, or swollen glands that may be enlarged for more than 3 months. Other symptoms often experienced months to years before the onset of AIDS include Lack of energy, Weight loss, Frequent fevers and sweats, Persistent or frequent yeast infections (oral or vaginal), Persistent skin rashes or flaky skin, Pelvic inflammatory disease in women that does not respond to treatment, Short-term memory loss and HIV related "Dementia".

Some people develop frequent and severe herpes infections that cause mouth, genital, or anal sores or a painful nerve disease called shingles. Children may grow slowly or get sick frequently.

At present the therapy for the treatment of HIV includes the antiretroviral compounds either single or in combination. Vaccine which is still under the research work and Somewhat the alternative medicines like use of medicinal plants or compounds obtained from them but all of them are having one or more limitations like,

- Incase of the antiretroviral therapy, they are more or less highly selective and also prone to develop resistance with time and also induce numerous side effects on long term uses.
- Incase of vaccine, it is not that much successful because the virus is capable of changing the outer structure configuration which lead to no effect of vaccine on the modified structure.
- Incase of the herbal therapy, till date so many tried and came with so many compositions but majorities of them are just the polyherbal formulation containing large no. of herbs combined together without any justification or optimization of the activity.

WO 02/20554 describes a novel and modified peptides capable of inducing a HIV-1 specific immune response without antagonizing the cytotoxic T-cell activity in order to achieve an effective prophylactic and therapeutic vaccine against HIV.

WO 2006/013106 discloses a HIV polypeptide and polynucleotide fusions of Gag, Pol and Nef which are useful in immunogenic compositions and vaccines.

WO2005/030232 describes six herbal compositions for effective treatment of HIV and AIDS are provided to reduce their hardships, method for preparation thereof and a method for the treatment of AIDS using said compositions.

WO 2005/021726 describes an immunogenic composition containing an HIV antigen, an immunomer and an adjuvant which enhances the duration and strength of the immune response in a mammal.

JP6040930 discloses an anti-AIDS viral agent comprising an extract of a plant belonging to the genus *Sindora, Helicteres, Swietenia, Andrographis, Curcuma* or *Loranthus* as an active ingredients.

WO2006118553 pertains to compositions for the treatment of HIV-related opportunistic infections and complications. More specifically, directed to a composition comprising Zanthoxylum gillettii and Anogeissus leiocarpus, in combination with citrus juice, or biomass extracts isolated therefrom, and methods of using and manufacturing the same Other than the above prior arts there are number of literatures which describe the treatment therapy for the HIV/AIDS but no therapy for the HIV/AIDS exists which is able to remove the HIV antigen glycoproteins which makes this disease silent killer.

Hence the need arise to develop the formulation or composition which can safely and effectively removes the HIV antigen glycoproteins without any major side effects.

Inventor of the present invention has surprisingly invented the bioactive composition which is able to remove the HIV antigen glycoproteins and thereby treat the HIV/AIDS without any major side effects.

OBJECT OF THE INVENTION

The main object of the present invention is to provide a bioactive composition which is able to remove the HIV antigen glycoproteins comprising bioactive compounds like curcumin, cyprenone, ursolic acid optionally combined with vinflunine, berberin sulfate and other additives.

One more object of the present invention is to provide the composition comprising curcumin, cyperone, ursolic acid and vinflunine with other additives.

Yet another object of the present invention is to provide the composition comprising curcumin, cyperone, ursolic acid and berberine sulfate with other additives.

One object of the present invention is to provide the composition comprising curcumin, cyperone, ursolic acid, vinflunine and berberine sulfate with other additives.

Another object of the present invention is to develop the method for preparation of the bioactive composition using curcumin, cyprenone, ursolic acid optionally combined with vinflunine, berberin sulfate and other additives.

Yet another object of the present invention is to use of this novel bioactive composition for the treatment of HIV/AIDS by administering to the patient in need thereof.

SUMMARY OF THE INVENTION

The present invention is all about a novel bioactive composition for the treatment of HIV which particularly produces its effect by removal of the most prominent HIV antigen glycoproteins. The novel plant bioactive composition comprises mainly curcumin, cyprenone, ursolic acid combined optionally with vinflunine and berberine sulfate as active components with other additives. The present invention further related to method of manufacturing and using such composition.

DETAILED DESCRIPTION OF THE INVENTION

The term "HIV antigen glycoproteins" as used herein is referred to glycoproteins which are obtained from mitogenically stimulated cultures in which tissue from AIDS patients are co-cultured with cells derived from non-AIDS patients, usually established leukemic cell lines. Following the detection of the reverse transcriptase enzyme in the culture, the supernatant, and more often cell lysates, are spun in density gradients. Material which bands at 1.16 gm/ml is considered to represent "pure HIV" and consequently the glycoproteins found at that density are considered to be HIV antigens. The immunogenic HIV glycoproteins are thought to be coded by three genes, namely gag, poi and env. The, gag gene codes a precursor p35/55, which is then cleaved to p24/25 and p17/18. The pol gene codes for p31/32, and the env gene codes the precursor glycoproteins p160 which is cleaved to p120 and p41/45, further, p66 endonuclease.

The p120 protein: The generally accepted view is that p120 and p41 are cleavage products of p160, which is found only in infected cells and not in the virus. However, p120 is a component only of the knobs (spikes) on the surface of HIV particles; The knobs are found only in the budding (immature) particles; and not in cell free (mature) particles; immature particles are "very rarely observed". Despite these findings, when "purified HIV" is tested against AIDS sera, strong bands corresponding to p120 and p160 develop. The solution to these contradictions was found when it was shown that p80 (vide infra) and "the components visualized in the 120-160-kDa region do not correspond to gp120 or its precursor but rather represent oligomers of gp41".

The p41 protein: p41 is one of the proteins detected by both Gallo's and Montanez's groups in the first HIV isolates. However, Montagnier and his colleagues observed that AIDS sera reacted with a p41 protein both in HIV and HTLV-I infected as well as non-infected cells, and concluded that the p41 band "may be due to contamination of the virus by cellular actin which was present in immunoprecipitates of all the cell extracts". Although Gallo's group did not find such reaction with p41 in non-infected cells, they did find a p80 protein and concluded that the reaction was "non-specific". Actin is a ubiquitous protein which is found in all cells as well as bacteria and several viruses. Well known retroviruses such as the mouse mammary tumour virus and Rous sarcoma virus have also been shown to contain actin of cellular origin and it has been postulated that this protein plays a key role in both retroviral assembly and budding. It is also known that oxidation of cellular sulfhydryl groups, as is the case in AIDS patients, is correlated with assembly of polymerised actin, and that the level of actin antibody binding to cells is determined by the physiological state of the cells. For this reason actin antibody binding to cells has been proposed "as a sensitive marker for activated lymphocytes". Platelets from healthy individuals also contain a p41/45 protein which reacts with sera from homosexual men with AIDS and immune thrombocytopenicpurpura (ITP) and which "represents non-specific binding of IgG to actin in the platelet preparation".

The p32 protein: In 1987 Henderson isolated the p30-32 and p34-36 of "HIV purified by double banding" in sucrose density gradients. By comparing the amino-acid sequences of these proteins with Class II histocompatibility DR proteins, they concluded that "the DR alpha and beta chains appeared to be identical to the p34-36 and p30-32 proteins respectively"

The p24/25 protein: Detection of p24 is currently believed to be synonymous with HIV isolation and viraemia. However, Apart from a joint publication with Montagnier where they claim that the HIV p24 is unique, Gallo and his colleagues have repeatedly stated that the p24s of HTLV-I and HIV immunologically cross-reaction conducted WB assays in 100 ELISA negative samples of healthy blood donors; 20 were found to have HIV bands which did not fulfil the then (1989) criteria used by the blood banks for a positive WB. These were considered as indeterminate WB, (WBI), with p24 being the predominant bands, (70% of cases). Among the recipients of WBI blood, 36% were WBI 6 months after transfusion, but so were 42% of individuals who received WB-negative samples. Both donors and recipients of blood remained healthy. They concluded that WBI patterns "are exceedingly common in randomly selected donors and recipients and such patterns do not correlate with the presence of HIV-1 or the transmission of HIV-1", "most such reactions represent false-positive results"; Antibodies to p24 have been detected in 1 out of 150 healthy individuals, 13% of randomly selected otherwise healthy patients with generalized warts, 24% of patients with cutaneous T-cell lymphoma and prodrome and 41% of patients with multiple sclerosis. Ninety-seven percent of sera from homosexuals with ITP and 94% of sera from homosexuals with lymphadenopathy or AIDS contain an antibody that reacts with a 25 Kd membrane antigen found in platelets from healthy donors and AIDS patients, as well as a 25 Kd antigen found in green-monkey kidney cells, human skin fibroblasts, and herpes simplex cultured in monkey kidney cells. This reaction was absent in sera obtained from non-homosexual patients with ITP or non-immune thrombocytopenic purpura. Conversely, the p24 antigen is not found in all HIV positive or even AIDS patients. In one study, the polymerase chain reaction (PCR) and p24 were used to detect HIV in patients at various CDC stages from asymptomatic to AIDS. p24 was detected in 24% patients and HIV RNA in 50%.

In another study, "In half of the cases in which a subject had a positive p24 test, the subject later had a negative test without taking any medications that would be expected to affect p24 antigen levels . . . the test is clinically erratic and should be interpreted very cautiously".

The p17/18 protein: In addition to the p24 band, the p17/18 band is the most often detected band in WB of healthy blood donors. Although, p17, Matrix Protein is considered as the prime glycoprotein to progress towards severe condition of HIV infection and the learned scientific community is focusing their attention on MA p17 which has notorious role in the HIV infected. HIV-1 replication is a dynamic process influenced by a combination of viral and host factors. The HIV-1 matrix protein p17 is a structural protein critically involved in most stages of the life cycle of the retrovirus. It participates in the early stages of virus replication as well as in RNA targeting to the plasma membrane, incorporation of the envelope into virions and article assembly. Besides its well established functions, p17 acts as a viral cytokine that works on preactivated—but not on resting—human T cells promoting proliferation, proinflammatory cytokines release and HIV-1 replication after binding to a cellular receptor (p17R). Thus, p17 might play a key role in the complex network of host- and Virus-derived stimulatory factors contributing to create a favourable environment for HIV-1 infection and replication.

Sera from AIDS patients bind to a p18 protein in mitogenically stimulated HIV infected, T-cells, but not to non-infected, unstimulated lymphocytes. However, when the lymphocytes are mitogenically stimulated, but non-infected, the AIDS sera bind to a p18 protein in these non-infected lymphocytes.

A monoclonal antibody (MCA) to HIV p18 reacts with dendritic cells in the lymphatic tissues of a variety of patients with a number of non-AIDS related diseases; and the "same pattern of reactivity was present in normal tissue taken from uninfected individuals as in those taken from HIV positive subjects".

AIDS patients and those at risk have high levels of antibodies to the ubiquitous protein myosin, which has two subunits of molecular weights 18,000 and 25,000. In view of all the above evidence it is difficult to defend the view that the bands p41 (and thus p160 and p120), p32, p24 or p18 represent specific HIV proteins. Even if it could be shown that all these proteins are HIV specific, it cannot be automatically assumed that antibodies that react with each of these proteins are specific to HIV infection.

The term "bioactive composition" as used herein refers to the composition prepared from the compounds having the biological origin and having therapeutic activity. The bioactive composition as used herein used therein are selected from tablets, capsule, powder sachets, pellets, beads, microspheres, microcapsules, pills, lozenges, granules, solution, syrup, suspension, emulsion or injection. Preferably the bioactive composition is in the form of capsule, tablet or powder sachet.

The bioactive compositions as described herein may comprise of one or more additives selected from diluent, binder, disintegrant; lubricant and mixtures thereof.

Diluent may be selected from powdered cellulose, microcrystalline cellulose, silicified microcrystalline cellulose, starch, dibasic calcium phosphate, tribasic calcium phosphate, calcium carbonate, dextrose, kaolin, magnesium carbonate, magnesium oxide; sugars such as lactose or sucrose; sugar alcohols such as mannitol, sorbitol or erythritol; and mixtures thereof. Preferably the diluent is of selected from the sugar.

Binder may be selected from hydroxyethyl cellulose, hydroxypropyl cellulose, hydroxypropyl methylcellulose, carbomers, dextrin, ethyl cellulose, methylcellulose, gelatin, polymethacrylates, polyvinylpyrrolidone, pregelatinized starch, sodium alginate, gums, synthetic resins and the like. Preferably the binder to be used for the present bioactive composition is polyvinylpyrrolidine.

Disintegrant may be selected from croscarmellose sodium, sodium starch glycolate, pregelatinized starch, sodium carboxymethyl cellulose, microcrystalline cellulose, crosslinked polyvinylpyrrolidone and mixtures thereof. The disintegrant preferred for the present bioactive composition is croscarmellose sodium.

Lubricant may be selected from talc, metallic stearates such as magnesium stearate, calcium stearate, zinc stearate; colloidal silicon dioxide, finely divided silicon dioxide, stearic acid, hydrogenated vegetable oil, glyceryl palmitostearate, glyceryl monostearate, glyceryl behenate, polyethylene glycols, sodium stearyl fumarate, sodium benzoate, mineral oil, magnesium trisilicate; and mixtures thereof. The preferred lubricant for the present invention is metallic stearate.

Granulating solvent may be selected from water, isopropyl alcohol, ethanol, methanol, acetone, methylene chloride or mixtures thereof. Preferred granulating solvent for the present invention is isopropyl alcohol either alone or in combination with water.

The term "bioactive compound" as used herein refers to the therapeutically active component obtained from any part of the plant by any known process. The bioactive compounds as used herein may be in dry powder form or oleo resin form.

Curcumin is a bioactive compound found in rhizomes of *Curcuma longa*. Chemically 1, 7-Bis (4-hydroxy-3-methoxyphenyl)-1,6-heptadiene-3,5-Dione having structural formula as given below.

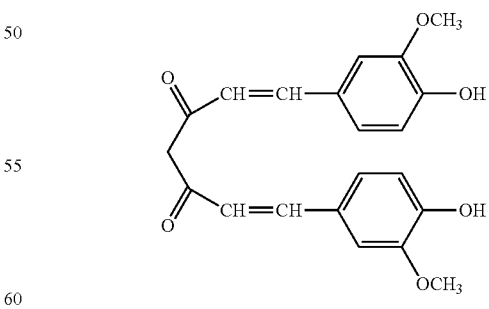

Curcumin is principal curcuminoid of the *Curcuma longa* having appearance of bright yellow to orange powder.

Curcumin incorporates several functional groups. The aromatic ring systems, which are polyphenols, are connected by two α, β-unsaturated carbonyl groups. The two carbonyl groups form a diketone. The diketone form stable enols or are easily deprotonated and form enolates, while α, β-unsaturated carbonyl is a good Michael acceptor and undergoes nucleophilic addition.

Cyperone is a bioactive compound found in rhizomes of *cyperus rotundus*. Chemically known as (4aS, 7R)-1,4a-Dimethyl-7-prop-1-en-2-yl-3,4,5,6, 7, 8-hexahydronaphthalen-2-one; (4aS-cis)-4,4-a,5,6,7,8-Hexahydro-1,4a-dimethyl-7-(1-methylethenyl)-2(3H)-naphthalenone having chemical structure as given below.

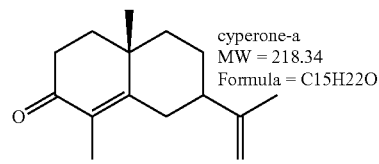 [SMILES: C=C(C)C1CC[C@@]2(C)CCC(=O)C(C)=C2C1]

Ursolic acid is a bioactive compound found in the leaves of Ocimum sanctum. Chemically known as (1S,2R,4aS,6aR,6aS,6bR,8aR,10S,12aR,14bS)-10-hydroxy-1,2,6a,6b,9,9,12a-hept amethyl-2,3,4,5,6,6a,7,8,8a,10,11,12,13,14b-tetradecahydro-1H-picene-4a-car boxylic acid having chemical structure as given below.

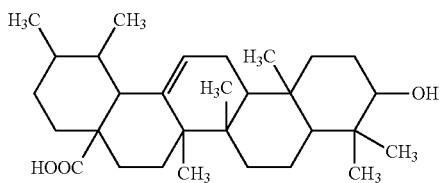

Vinflunine is a fluorinated vinca alkaloid found in leaves and roots of Vinca rosea having chemical structure as given below.

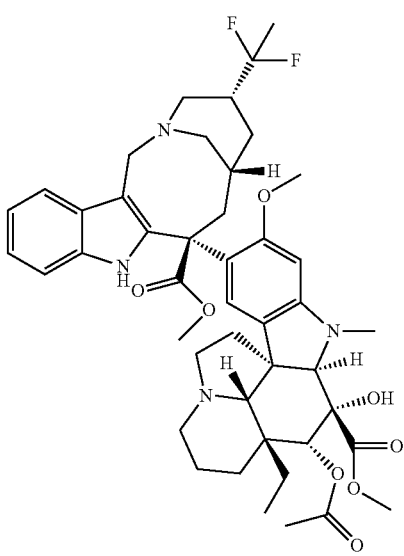

Berberine sulfate is an alkaloid that is extracted from the roots of a number of traditionally used medicinal plants; these include Hydrastis canadensis (goldenseal), Coptis chinensis (coptis), Berberis aquifolium (Oregon grape), Berberis vulgaris (barberry), and Berberis aristata (tree turmeric).

The invention is described here in according to one of its preferred embodiments that are intended not to limit the invention, but to illustrate more clearly the bioactive composition according to present invention, and its related method of manufacturing and treatments.

EXAMPLES

Example 1

Bioactive Composition in Tablet Form

|  |  | % w/w | | |
|---|---|---|---|---|
| Sr. No | Ingredients | Example 1 | Example 2 | Example 3 |
| 1 | Curcumin | 30 | 15 | 10 |
| 2 | Cyperone | 15 | 25 | 45 |
| 3 | Ursolic acid | 25 | 35 | 15 |
| 4 | Vinflunine | 5 | 5 | 5 |
| 5 | Berberine sulfate | 5 | — | 5 |
| 6 | Lactose | 10 | 10 | 10 |
| 7 | Polyvinylpyrrolidone K-30 | 4 | 4 | 4 |
| 8 | Isopropyl alcohol | Qs | Qs | Qs |
| 9 | Croscarmellose sodium | 5 | 5 | 5 |
| 10 | Magnesium stearate | 1 | 1 | 1 |

Procedure:
(i) Mixing bioactive compounds of Sr. No. 1,2,3,4, and 5 with lactose
(ii) Granulating the mixture of step (i) with a granulating solution of PVP K-30 prepared in Isopropyl alcohol.
(iii) Drying the granules of step (ii),
(iv) Mixing the granules of step (iii) with CCS and magnesium stearate and
(v) Compressing the mixture of step (iv) into a tablet using appropriate punch tooling.

Example 2

Bioactive Composition in Capsule or Powder Sachet Form

|  |  | % w/w | | |
|---|---|---|---|---|
| Sr. No. | Ingredients | Example 4 | Example 5 | Example 6 |
| 1 | Curcumin | 60 | 20 | 15 |
| 2 | Cyperone | 15 | 55 | 20 |
| 3 | Ursolic acid | 15 | 20 | 55 |
| 4 | Vinflunine | 5 | 5 | 5 |
| 5 | Berberine sulfate | 5 | — | 5 |

Procedure
i) All ingredients are sifted through sieve and mixed together.
ii) Mixed blend of step i) is filled in hard gelatin capsule or the aluminium pouch.
iii) 'Aerosil' may be used to avoid moisture contents and to control pH value.

Example 3

Clinical Investigation
The pilot study to check the effectiveness of the bioactive composition in the HIV/AIDS patients has been conducted. Total 76 patients have been evaluated but six of them had been undertaken in pilot clinical trials to determine the clinical response of the bioactive composition in the HIV/AIDS affected patients to the administration of the bioactive composition.

The bioactive composition had been administered in dosing schedule of 2 units 2 times a day and all other conventional drugs were stopped for true outcome. Weight management, Blood Pressure, Diabetes, Mental position, Cardiac history, Hb, TCDC, Skin eruption, Dietary composition, renal and digestive tracks, Liver function, addiction history, sexual behaviour, surgical track records, thyroid functions, menustral position were observed with the reputed pathology laboratory alongwith HIV-1 & HIV-2: Western Blot Technique as well as CD4 absolute ratio.

Clinical summary

| Sr. No | Patient | Sex/Age | Tenure of assessment | Result | Major Side Effect |
|---|---|---|---|---|---|
| 1 | LP | M/33 | 4 months | →Removal of p24 | NIL |
| 2 | PP | F/26 | 5 months | →Removal of p17 | NIL |
| 3 | GR | M/26 | 9 months | →Removal of p31<br>→Removal of p66 | NIL |
| 4 | PS | M/38 | 13 months | →Removal of p51/55 & p24<br>→CD4 ratio boost up from 196 to 390 | NIL |
| 5 | GT1 | F/39 | 3 months | →Removal of p17<br>→CD4 ratio boost up from 279 to 414 | NIL |
| 6 | GT2 | M/42 | 3 months | →Removal of p17<br>→CD4 ratio boost from 105 to 173 | NIL |

After the current studies and the results obtained by the performed clinical assessment, it is confirmed that the bioactive composition according to the invention can be considered most reliable for the treatment of HIV/AIDS and that is also without any major side effects. During the clinical trials, weight gain of each patient was ranging from 2.5 Kg. to 16 Kg. during the course of four/five months. As weight loss is the prime symptom of HIV infected, hence the invented bioactive composition has shown to have its objected outcome with safety, efficacy and reliability. The periodical confirmation by the Western Blot test has shown its safe and effective outcome.

Although the present invention has been described according to one of the preferred embodiments, is not limited to the examples described here and alteration or variation can be possible without deviating from the protection of the present invention.

What is claimed is:

1. A bioactive composition comprising:
   a quantity of curcumin, wherein said quantity of curcumin is in the range of 10%-30% w/w;
   a quantity of cyperone, wherein said quantity of cyperone is in the range of 15%-45% w/w; and
   a quantity of ursolic acid, wherein said quantity of ursolic acid is in the range of 15%-35% w/w.

2. The bioactive composition of claim 1, wherein the composition further comprises:
   a quantity of vinfluine, wherein said quantity of vinfluine is 5% w/w; and
   a quantity of berberin sulfate.

3. The bioactive composition of claim 1, wherein the composition further comprises:
   a plurality of additives, wherein the additives are selected from the group consisting of dilutents, binders, disintegrants, lubricants, and mixtures thereof.

4. The bioactive composition of claim 3, wherein the dilutent is be selected from the group consisting of powdered cellulose, microcrystalline cellulose, silicified microcrystalline cellulose, starch, dibasic calcium phosphate, tribasic calcium phosphate, calcium carbonate, dextrose, kaolin, magnesium carbonate, magnesium oxide, sugars, sugar alcohols, and mixtures thereof.

5. The bioactive composition of claim 3, wherein the binder is selected from the group consisting of hydroxyethyl cellulose, hydroxypropyl cellulose, hydroxypropyl methylcellulose, carbomers, dextrin, ethyl cellulose, methylcellulose, gelatin, polymethacrylates, polyvinylpyrrolidone, pregelatinized starch, sodium alginate, gums, and synthetic resins.

6. The bioactive composition of claim 3, wherein the disintegrant is selected from the group consisting of croscarmellose sodium, sodium starch glycolate, pregelatinized starch, sodium carboxymethyl cellulose, microcrystalline cellulose, cross-linked polyvinylpyrrolidone and mixtures thereof.

7. The bioactive composition of claim 3, wherein the lubricant is selected from the group consisting of talc, magnesium stearate, calcium stearate, zinc stearate, colloidal silicon dioxide, finely divided silicon dioxide, stearic acid, hydrogenated vegetable oil, glyceryl palmitostearate, glyceryl monostearate, glyceryl behenate, polyethylene glycols, sodium stearyl fumarate, sodium benzoate, mineral oil, magnesium trisilicate, and mixtures thereof.

8. The bioactive composition of claim 1, wherein the composition is in a form selected from the group consisting of tablets, capsule, powder sachets, pellets, beads, microspheres, microcapsules, pills, lozenges, granules, solution, syrup, suspension, emulsion or injection.

9. The bioactive composition of claim 1, wherein the composition is utilized for the removal of a plurality of HIV antigen glycol proteins, selected from the group consisting of p120, p41, p32, p24/25 and p17/18.

10. The bioactive composition of claim 1, wherein each of the bioactive compounds is present in the form selected from the group consisting of dry powdered extract and oleo resin form.

11. A bioactive composition for the treatment of HIV/AIDS comprising:
    a quantity of curcumin, wherein said quantity of curcumin is in the range of 10% -30% w/w;
    a quantity of cyperone, wherein said quantity of cyperone is in the range of 15% -45% w/w ;
    a quantity of ursolic acid, wherein said quantity of ursolic acid is in the range of 15% -35% w/w;
    a quantity of vinflunine;
    a quantity of berberin sulfate; and
    a plurality of additives.

12. The bioactive composition of claim 11 for the treatment of HIV/AIDS, wherein the plurality of additives further includes:
    a dilutent;
    a binder;
    a disintegrant; and
    a lubricant.

13. A method of reducing HIV-associated glycoproteins and increasing CD4 counts in a patient having HIV/AIDS by administering a therapeutically effective bioactive composition as defined by claim 1.

14. A method for the production of the bioactive composition of claim 1, comprising the steps of:

a) mixing together a quantity of curcumin, cyperone and ursolic acid;
b) granulating the mixture;
c) drying the granules;
d) mixing the granules; and
e) compressing the mixture.

15. The method of claim 14, wherein the step of mixing together a quantity of curcumin, cyperone and ursolic acid further includes adding a plurality of additives to the mixture.

16. The method of claim 14, wherein the step of granulating the mixture further includes adding a granulating solvent.

17. The method of claim 16, wherein the granulating solvent is selected from the group consisting of water, isopropyl alcohol, ethanol, methanol, acetone, methylene chloride and mixtures thereof.

18. The method of claim 14, wherein the step of mixing the granules further includes adding a plurality of additives to the mixture.

19. The method of claim 14, wherein the step of compressing the mixture further includes compressing the mixture into a form selected from the group consisting of a tablet, capsule and sachet.

* * * * *